US00PP26582P2

(12) United States Plant Patent
Vlasveld

(10) Patent No.: US PP26,582 P2
(45) Date of Patent: Apr. 5, 2016

(54) ***HYDRANGEA* PLANT NAMED 'VLASVELD002'**

(50) Latin Name: *Hydrangea paniculata*
Varietal Denomination: Vlasveld002

(71) Applicant: Peter Vlasveld, Boskoop (NL)

(72) Inventor: Peter Vlasveld, Boskoop (NL)

( * ) Notice: Subject to any disclaimer, the term of this patent is extended or adjusted under 35 U.S.C. 154(b) by 52 days.

(21) Appl. No.: 14/120,079

(22) Filed: Apr. 23, 2014

(51) Int. Cl.
*A01H 5/02* (2006.01)

(52) U.S. Cl.
USPC ..... Plt./250

(58) Field of Classification Search
USPC ..... Plt./250
CPC ..... A01H 5/02; A01H 5/00
See application file for complete search history.

(56) References Cited

PUBLICATIONS http://www.esveld.nl/htmldiaen/h/hypcon.php; Aug. 24, 2012; 1 page.*

* cited by examiner

*Primary Examiner* — Kent L Bell
(74) *Attorney, Agent, or Firm* — Penny J. Aguirre

(57) ABSTRACT

A new cultivar of *Hydrangea paniculata,* 'Vlasveld002', that is characterized by its compact, narrow, and upright plant habit, its conical shaped panicle type inflorescences, its sterile flowers that are persistently white in color, its stems readily produce basal branches with one spring pruning, and its high tolerance to rain and wind.

2 Drawing Sheets

Genus/species: *Hydrangea paniculata.*
Varietal denomination: 'Vlasveld002'.

BACKGROUND OF THE INVENTION

The present invention relates to a new and distinct cultivar of *Hydrangea paniculata* and will be referred to hereafter by its cultivar name, 'Vlasveld002'. 'Vlasveld002' represents a new cultivar of panicled *hydrangea,* a deciduous shrub grown for landscape use and for use as a potted plant.

The new cultivar of *Hydrangea*, 'Vlasveld002', was discovered by the Inventor as a chance seedling in a trial garden in Boskoop, The Netherlands in July 2010. The exact parentage is unknown.

Asexual propagation of the new cultivar was first accomplished by the Inventor by softwood cuttings in 2011 in Boskoop, The Netherlands. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Vlasveld002' as a unique cultivar of *Hydrangea.*

1. 'Vlasveld002' exhibits a compact, narrow, upright plant habit.
2. 'Vlasveld002' exhibits conical shaped, panicle type inflorescences.
3. 'Vlasveld002' exhibits sterile flowers that are persistently bright white in color.
4. 'Vlasveld002' exhibits stems that branch readily with one spring pruning.
5. 'Vlasveld002' exhibit a high tolerance to rain and wind.

'Vlasveld002' can be most closely compared to the *Hydrangea paniculata* cultivars 'PIIHP-I' (U.S. Plant Pat. No. 23,387) and 'DVPpinky' (U.S. Plant Pat. No. 16,166). 'PIIHP-I' is similar to 'Vlasveld002' in having sterile flowers that are initially white in color. 'PIIHP-I' differs from 'Vlasveld002' in having a rounded plant habit, in having foliage that is dark green in color, and in having sterile flowers that fade to a reddish tinged green color. 'DVPpinky' is similar to 'Vlasveld002' in having conical shaped inflorescences and sterile flowers that are initially white in color. 'DVPpinky' differs from 'Vlasveld002' in having a more outwardly spreading plant habit, in having wider inflorescences, in being less branched, and in having sterile flowers that fade to a dark pinkish red to purple-red color.

BRIEF DESCRIPTION OF THE DRAWINGS

The accompanying colored photographs illustrate the overall appearance and distinct characteristics of a one year-old plant of the 'Vlasveld002', as grown outdoors in a 5-liter container in Boskoop, The Netherlands.

The photograph in FIG. 1 provides a side view of the overall plant habit of a plant of 'Vlasveld002'.

Figure 1:
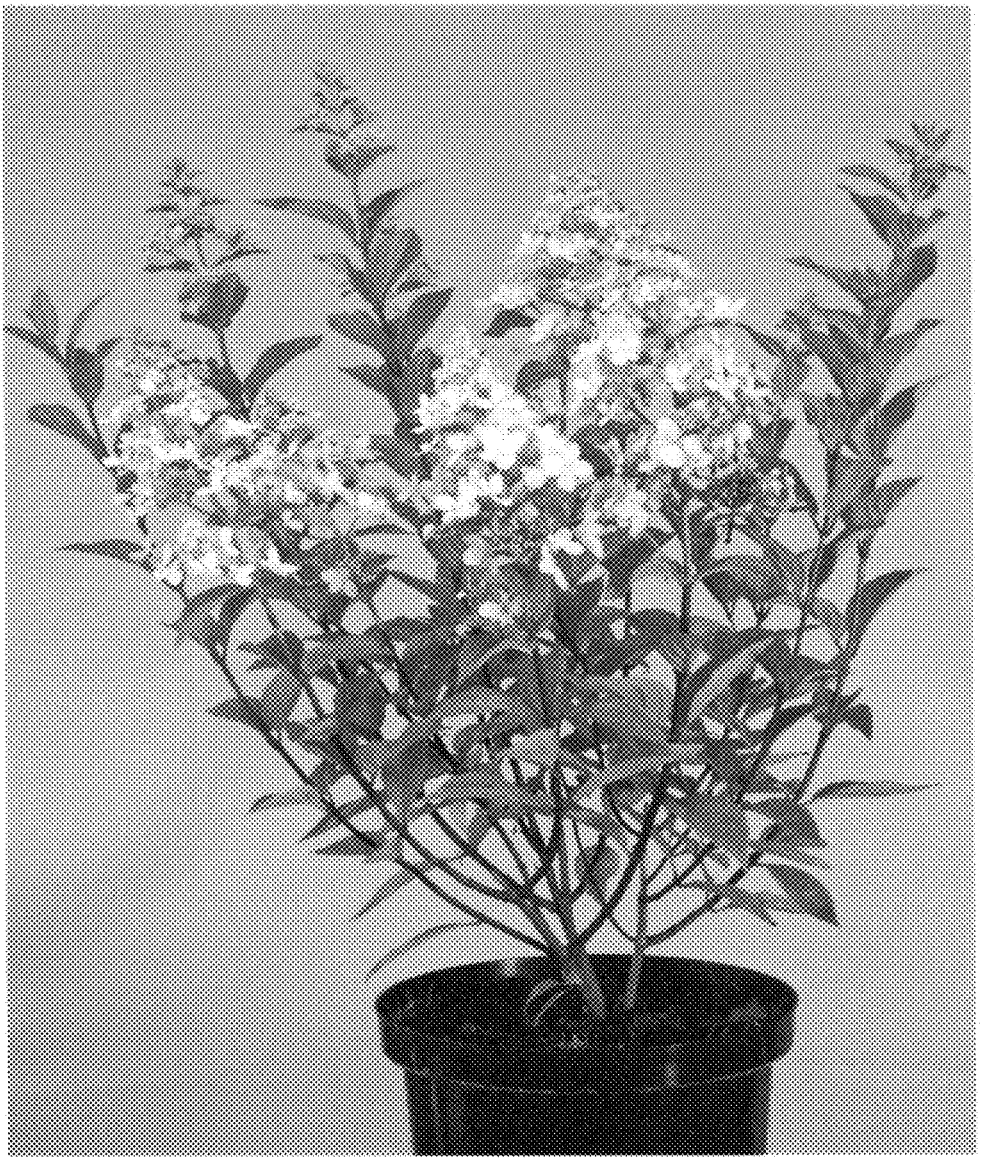
Figure 2:
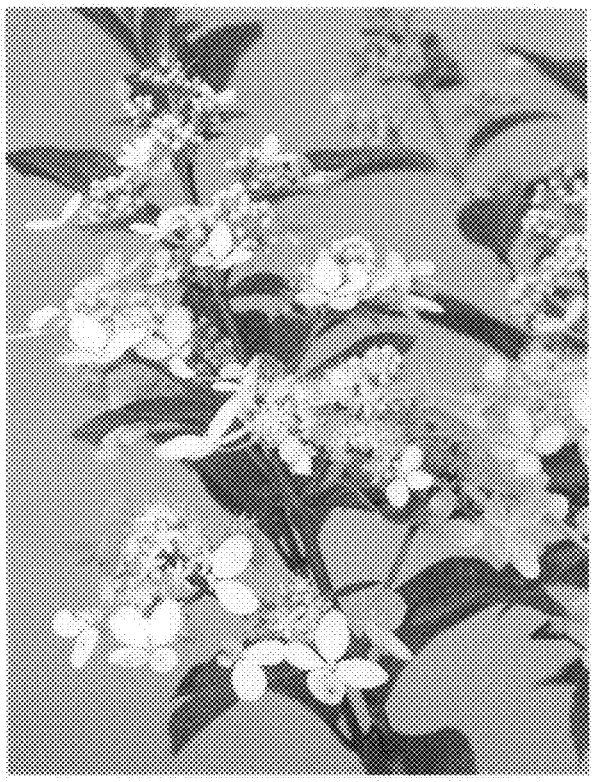

The photograph in FIG. 2 provides a close-up view of an inflorescence of 'Vlasveld002'.

Figure 3:
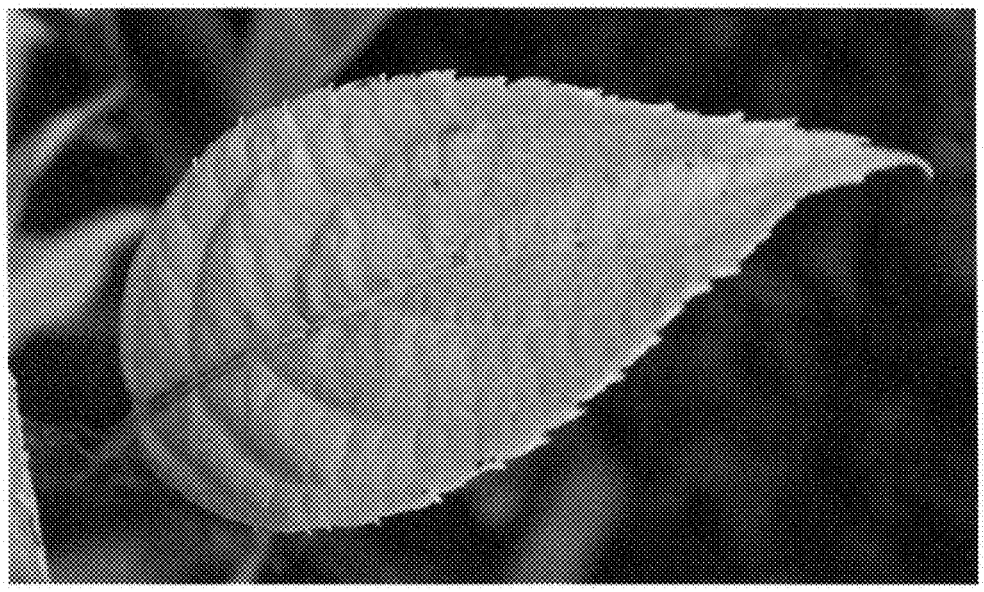

The photograph in FIG. 3 provides a close-up view of a leaf of 'Vlasveld002'.

The colors in the photographs may differ slightly from the color values cited in the detailed botanical description, which accurately describe the colors of the new *Hydrangea.*

BOTANICAL DESCRIPTION OF THE PLANT

The following is a detailed description of the new cultivar as observed on a one year-old plant as grown outdoors in 5-liter containers in Boskoop, The Netherlands. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period*.—Summer to early autumn in Boskoop, The Netherlands.

*Plant habit*.—Compact, narrow, and upright.

*Height and spread*.—An average of 52.5 cm in height and 50.3 cm in spread.

*Hardiness*.—At least in U.S.D.A. Zones 4 to 9.

*Diseases and pests*.—No particular susceptibility or resistance to diseases or pests has been observed.

*Environmental conditions*.—Observed to be highly tolerant.

*Root description*.—Fibrous and fine.

*Propagation*.—Softwood cuttings.

*Growth rate*.—Moderate.

Stem description:

*Shape shape*.—Rounded.

*Stem color*.—New wood; 144B, sunny side 180A, mature wood; 200C, later becoming 199B to 199C.

*Stem size*.—Average of 32.7 cm in length (excluding inflorescence) and 4 mm in diameter.

*Stem surface*.—Glabrous.

*Stem aspect*.—Average angle 50° (soil level=0°), tips in an average angle of 75°.

*Internode length*.—Average of 4.2 cm.

*Branching*.—Average of 17 basal branches, free branched from the base with single hard pruning.

Foliage description:

*Leaf shape*.—Ovate to narrow ovate.

*Leaf division*.—Simple.

*Leaf size*.—Average of 7.2 cm in length and 3.5 cm in width.

*Leaf base*.—Rounded to short attenuate.

*Leaf apex*.—Acute to short apiculate.

*Leaf venation*.—Pinnate, color upper surface; 152C, color lower surface; 147D, tinged 182B towards the base.

*Leaf margins*.—Serrated.

*Leaf attachment*.—Petiolate.

*Leaf arrangement*.—Opposite.

*Leaf surface*.—Both surfaces sparsely covered with very short adpressed strigose hairs, lower side mainly on the main vein and secondary veins, hairs are 0.5 mm in length and NN155C to NN155D in color.

*Leaf color*.—Immature leaves upper surface; 143C, immature leaves lower surface; 145A, mature leaves upper surface; 144A, mature leaves lower surface; between 144C and 146D.

*Petioles*.—Average of 9 mm in length and 2 mm in diameter, upper surface; 178B to 178C in color, upper surface; matte and moderately covered with pubescence of very short hairs an average of 0.3 mm in length and 156D in color, lower surface; matte and glabrous and a color between 147D and 195C.

Inflorescence description:

*Inflorescence type*.—Terminal panicle.

*Lastingness of inflorescence*.—Persistent with color lasting from summer to early autumn.

*Inflorescence number*.—One per lateral or sublateral stem.

*Inflorescence size*.—Average of 16.9 cm in depth and 11.3 cm in diameter.

*Flower number*.—Average of 80 sterile flowers and 800 fertile flowers per panicle.

*Flower fragrance*.—Faint to moderate, sweet and pleasant.

*Flower aspect*.—Sterile flowers; upright, more outward when aging, fertile flowers; upright to outward.

*Flower size*.—Sterile flowers; an average of 2.5 cm in diameter and 8 mm in depth, fertile flowers; an average of 8 mm in diameter and 5 mm in depth.

*Flower type*.—Rotate.

*Flower buds*.—Sterile flowers; average of 6 mm in length and 4 mm in diameter, ovate in shape, 150D in color, fertile flowers; average of 3.5 mm in length and 2 mm in width, broadly obovate in shape, NN155D with base 157D and apex 68B.

*Peduncles*.—Strong, an average of 4 cm in length and 4 mm in width, a blend of 144B and 180A in color, surface glabrous.

*Pedicels*.—Sterile flowers; held at a 55° angle from vertical, an average of 1.3 cm in length and 1 mm in width, moderate strength, NN155A in color, dull, moderately pubescent surface covered with adpressed hairs 0.3 mm in length and NN155D in color, fertile flowers; held at all angles, an average of 2 mm in length and 0.5 mm in diameter, moderate strength, dull, glabrous surface, NN155D in color.

*Petals*.—Fertile flowers; average of 5, rotate in arrangement, ovate in shape, entire margin, acute apex, broad cuneate base, average of 3 mm in length and 1.5 mm in width, upper surface glabrous and moderately glossy, lower surface glabrous and matte, color; upper surface when opening NN155D, lower surface when opening NN155D suffused with 68B, upper surface when fully opened NN155D, lower surface when fully opened NN155D suffused with 68C to 68D, color is not fading, self-cleaning, sterile flowers; average of 4, rotate in arrangement, ovate and concave in shape, an average of 2.5 cm in length and 1.5 cm width, broadly acute apex, cuneate base, entire margins, slightly glossy and glabrous on upper surface, matte and glabrous lower surface, color: when opening upper surface; NN155C to NN155D, when opening lower surface NN155A, upper half 68A to 68B, when fully open upper surface NN155C, when fully open lower surface NN155A, upper half 68B, non-fading and non-persistent.

*Sepals*.—Sterile flowers; average of 4, rotate in arrangement, ovate to elliptic, occasionally obovate in shape, an average of 1.5 cm in length and 1 cm width, obtuse to rounded apex, cuneate base, entire margins, matte and glabrous on upper and lower surface, color: upper surface when opening a blend of 155A, 155B and 157D, lower surface when opening 155B, upper surface when fully open upper surface 155A, lower surface when fully open 155B, upper surface fading to 155A and moderately tinged 186C towards the base, lower surface fading to 155A to 155B, fertile flowers; average of 5, short triangular in shape, entire margin, broad acute apex, broad cuneate base, average of 0.5 mm in length and 1 mm in width, upper surface glabrous and slightly glossy, lower surface texture is glabrous and matte, color of upper and lower surface when opening and when fully open 157D, color not fading.

Reproductive organs: (Fertile flowers perfect, male flowers staminate)

*Stamens*.—Sterile flowers; average of 8, filament is 2 mm in length and NN155D in color, anther is double kidney-shaped, 0.04 mm in length and 155A in color, pollen amount is low and 158D in color, fertile flowers; average of 10, filament is 3 mm in length and NN155D in color, anther is double kidney-shaped, 0.04 mm in length and 155A in color, pollen amount is low and 158D in color.

*Pistils*.—Sterile flowers; no gynoecium present in sterile flowers, fertile flowers; average of 2, occasionally 3, an average of 1.5 mm in length, stigma is flattened on top of style and 156D in color, style is an average of 1 mm in length and 157A in color, ovary is between 155A and 157D in color.

*Fruit and seed*.—Has not been observed to date.

It is claimed:

1. A new and distinct cultivar of *Hydrangea* plant named 'Vlasveld002' as herein illustrated and described.

* * * * *